United States Patent [19]

Koehler et al.

[11] Patent Number: 5,132,427

[45] Date of Patent: Jul. 21, 1992

[54] PROCESS FOR THE PREPARATION OF AMINES

[75] Inventors: Ulrich Koehler, Heidelberg; Hardo Siegel, Speyer; Peter Jaeger, Battenberg; Matthias Irgang, Heidelberg, all of Fed. Rep. of Germany

[73] Assignee: BASF Aktiengesellschaft, Ludwigshafen, Fed. Rep. of Germany

[21] Appl. No.: 600,727

[22] Filed: Oct. 22, 1990

[30] Foreign Application Priority Data

Oct. 21, 1989 [DE] Fed. Rep. of Germany ....... 3935112

[51] Int. Cl.$^5$ .................. C07D 211/27; C07C 209/48
[52] U.S. Cl. .................................. 546/246; 564/491; 564/512
[58] Field of Search ............... 546/246, 320, 329, 336; 564/491, 490

[56] References Cited

U.S. PATENT DOCUMENTS 3,246,000 4/1966 Baizer et al. ................ 564/320
4,943,549 7/1990 Immel et al. ................ 502/304

FOREIGN PATENT DOCUMENTS 62-270550 5/1986 Japan .
62-273938 11/1987 Japan .

OTHER PUBLICATIONS

Chem. Abstracts, vol. 91 (1979), p. 598; (CA 91:19880n, Oshima et al.).

Primary Examiner—Glennon H. Hollrah
Assistant Examiner—Shailendra Kumar
Attorney, Agent, or Firm—John H. Shurtleff

[57] ABSTRACT

A process for the preparation of amines of the formula

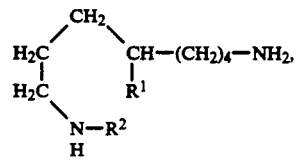

in which $R^1$ is the radical $H_2N\text{-}CH_2$ and $R^2$ is hydrogen, or $R^1$ and $R^2$ together form a bridging group $-CH_2-$, by reacting 1,3,6-tricyanohexane at elevated temperature and pressure with hydrogen in contact with a catalyst containing, in addition to cobalt oxide, and oxide of an alkali metal, an oxide of an alkaline earth metal, an oxide of a rare earth or an oxide of scandium or yttrium.

15 Claims, No Drawings

PROCESS FOR THE PREPARATION OF AMINES

This invention relates to a novel process for the preparation of the amines 4-aminomethyl-1,8-diaminooctane and/or 3-(4-aminobutyl)-piperidine by the catalytic hydrogenation of 1,3,6-tricyanohexane.

4-Aminomethyl-1,8-diaminooctane and 3-(4-aminobutyl)-piperidine are valuable intermediates. For example, 4-aminomethyl-1,8-diaminooctane is used as a curing agent for epoxides or for the preparation of pesticides, whilst 3-(4-aminobutyl)-piperidine is an interesting compound for the preparation of nicotinic acid.

It is known that 4-aminomethyl-1,8-diaminooctane and 3-(4-aminobutyl)-piperidine can be prepared by catalytic hydrogenation of 1,3,6-tricyanohexane. For example, when 1,3,6-tricyanohexane is hydrogenated in contact with Raney cobalt, mixtures of 4-aminomethyl-1,8-diaminooctane and 3-(4-aminobutyl)-piperidine are obtained. This process, which is described in U.S. Pat. No. 3,246,000, produces a fairly high residue of non-distillables. According to Example 2 of said patent specification, this residue is 23%. Selective preparation of 4-aminomethyl-1,8-diaminooctane and 3-(4-aminobutyl)-piperidine is not possible. Better results are obtained by hydrogenation in contact with Raney cobalt in the presence of water, as described in JP 62 270,550. By this method, 4-aminomethyl-1,8-diaminooctane is obtained in a yield of 70%. When 1,3,6-tricyanohexane is hydrogenated in contact with Raney nickel in the presence of alkali metal hydroxide in alcohol, 4-aminomethyl-1,8-diaminooctane is obtained in a yield of 92%, according to JP 62 273,938.

However, the two last-named methods suffer from the drawback that it is not possible to steer the synthesis preferentially in favor of 4-aminomethyl-1,8-diaminooctane or 3-(4-aminobutyl)-piperidine. In addition, the yields are not satisfactory and the methods tend to be more suitable for batchwise operation.

Thus the problem to be solved was to provide a process for the preparation of 4-aminomethyl-1,8-diaminooctane and/or 3-(4-aminobutyl)-piperidine in an advantageous and highly economical manner. More over, the novel process should make it possible to select which of the two amines is to be synthesized. Continuous operation is desirable and the catalysts used should contain cheap non-noble metals and have a long useful life.

According to the process of the invention, which satisfies the above requirements to a large extent, amines of the formula

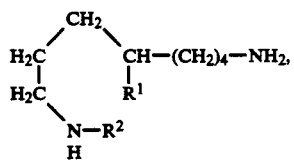

in which $R^1$ is the radical $H_2N-CH_2$ and $R^2$ is hydrogen, or $R^1$ and $R^2$ together form a bridging group $-CH_2-$, are prepared by reacting 1,3,6-tricyanohexane at elevated temperature and pressure with hydrogen in contact with a catalyst containing cobalt oxide, wherein the catalyst used is one which contains, in addition to cobalt oxide, an oxide of an alkali metal, an oxide of an alkaline earth metal, an oxide of a rare earth or an oxide of scandium or yttrium.

In our novel process, hydrogenation is carried out at a temperature of, say, from 30° to 250° C. and under a pressure of, say, from 50 to 350 bar. The catalyst used is one which contains, in addition to cobalt oxide, an oxide of an alkali metal, an oxide of an alkaline earth metal, an oxide of a rare earth or an oxide of scandium or yttrium. Examples of alkali metal and alkaline earth metal oxides are $LiO_2$, $Na_2O$, $K_2O$, $MgO$, $CaO$, $SrO$ and $BaO$. Oxides of rare earths which may be used are, for example, $La_2O_3$, $Ce_2O_3$, $Gd_2O_3$, $Dy_2O_3$, $Sm_2O_3$, $Nd_2O_3$ and $Er_2O_3$. The catalytically active material contains cobalt oxide as the main component and, as secondary component, at least one of the metal oxides stated above. For example, the catalytically active material has a content of from 20 to 95% w/w of cobalt oxide and from 0.5 to 20% w/w of said oxides. Preferably, the catalyst contains, in addition to cobalt oxide and an oxide of an alkali metal, an oxide of an alkaline earth metal, an oxide of a rare earth or an oxide of scandium or yttrium, an oxide of one or more of the elements iron, nickel, manganese, chromium, molybdenum, tungsten and phosphorus, of which iron, nickel and manganese are preferred.

Particularly suitable catalysts are, for example, those of which the catalytically active material contains at least 20% w/w of cobalt oxide, not more than 20% w/w of an oxide of an alkali metal, an oxide of an alkaline earth metal, an oxide of a rare earth or an oxide of scandium or yttrium and up to 60% w/w of an oxide of one or more of the elements iron, nickel, manganese, chromium, molybdenum, tungsten and phosphorus. Examples of such catalysts are those of which the catalytically active material contains from 20 to 95% and preferably from 40 to 90%, by weight, of cobalt oxide, from 0.5 to 20% w/w of an oxide of an alkali metal, an oxide of an alkaline earth metal, an oxide of a rare earth or an oxide of scandium or yttrium and from 0.5 to 60% and preferably from 1 to 40%, by weight, of an oxide of manganese, nickel or iron.

The catalysts may be in the form of solid catalysts, i.e. powders or granules, or in the form of supported catalysts, in which case the inert support may comprise, for example, silicon dioxide, aluminum oxide, zeolites, titanium dioxide, magnesium oxide, pumice, zirconium oxide or carbon. The catalyst containing the metal components in the form of their oxides is usually activated, before use, by treatment with hydrogen, by which means the oxides are partially reduced to the metals.

The 1,3,6-tricyanohexane is used as such or dissolved in a solvent. Suitable solvents are, for example, ethers such as tetrahydrofuran or dioxane, alcohols such as methanol or ethanol, or other solvents conventionally used in hydrogenations, e.g. dimethyl formamide or N-methylpyrrolidone.

The hydrogenation is carried out batchwise or, preferably, continuously in a fixed-bed reactor (trickle-bed reactor or packed bubble column) or in suspension. When operating batchwise, the procedure may be, for example, to place the 1,3,6-tricyanohexane or solution thereof in a high-pressure autoclave together with the catalyst and then to pump in ammonia and hydrogen and heat the reaction mixture. On completion of the reaction, the reaction mixture is cooled and, after removal of the catalyst, subjected to fractional distillation.

The hydrogen employed for the hydrogenation is generally used in relatively large stoichiometric excess.

It may be recycled to the reaction. The hydrogen used is generally industrially clean, but inert impurities, such as nitrogen, have no adverse influence on the course of the reaction.

The process of the invention offers the possibility of selecting the synthesis of one or other of the two possible reaction products. If it is preferred to synthesize 4-aminomethyl-1,8-diaminooctane, the hydrogenation will be carried out at as low a temperature as possible, i.e. a temperature of from 30° to 120° C. and preferably from 50° to 100° C. Under these conditions it is advantageous to add ammonia at the rate of 1 to 100 moles per mole of 1,3,6-tricyanohexane to further inhibit the formation of 3-(4-aminobutyl)-piperidine.

If it is desired to synthesize 3-(4-aminobutyl)-piperidine, the hydrogenation is carried out at as high a temperature as possible, i.e. a temperature above 120° and up to 250° C., preferably between 120° and 200° C. In this case little or no ammonia is used (0 to 3 moles per mole of trinitrile). In both cases, hydrogenation is carried out within the pressure range stated above.

The process of the invention makes it possible to vary the ratio of the two reaction products 4-aminomethyl-1,8-diaminooctane and 3-(4-aminobutyl)-piperidine such that it ranges from 98:2 to 2:98.

For example, when operating continuously at a temperature of 60° C., a pressure of 300 bar of hydrogen, a ten times molar excess of ammonia and a throughput rate of 0.05 kg/l.h, the discharged reaction mixture contains 97.9% w/w of 4-aminomethyl-1,8-diaminooctane and 1.8% w/w of 3-(4-aminobutyl)-piperidine, whereas at 170° C. under otherwise identical conditions but not using ammonia, the yield comprises 1.8% w/w of 4-aminomethyl-1,8-diaminooctane and 97.8% w/w of 3-(4-aminobutyl)-piperidine (Example 5). The novel process produces the desired products in virtually quantitative yield and at relatively high space-time yields. The on-stream times (for continuous operation) are longer than 2 months.

In the following Examples the percentages are by weight.

EXAMPLES

Example 1

Preparation of Suitable Catalysts

Catalyst A (powder)

An aqueous solution containing cobalt nitrate, iron nitrate and manganese nitrate and a 30% aqueous sodium bicarbonate solution are metered separately to a stirred vessel such that a constant pH of 6.5 is maintained. The temperature in said precipitation vessel is kept at 50° C.

The precipitated product is pumped to a filter press and washed free of sodium. The filter paste is then mixed with finely ground calcium hydroxide powder in a mixer, and the mixture is dried and calcined at 500° C. Finally, it is milled to a particle size of from 0.05 to 0.2 mm. There is obtained a catalyst having the following chemical composition (calculated as being free from loss at red heat):

65.2% of CoO
4.7% of $Mn_3O_4$
10.0% of CaO
20.1% of $Fe_2O_3$.

Catalyst B (extrudates)

Starting from an aqueous solution containing cobalt nitrate, iron nitrate, nickel nitrate and manganese nitrate, a catalyst precursor is precipitated with soda solution, filtered and washed as described above under Catalyst A.

The filter paste is mixed with calcium hydroxide powder (10% CaO, based on the total oxides) in a mixer and is then dried and calcined at 500° C. The product thus obtained is compressed in a kneader until it has a plastic consistency. It is then extruded, dried and calcined again, at 650° C. The 4 mm extrudates have the following chemical composition (calculated as being free from loss at red heat):

69.2% of CoO
4.9% of $Mn_3O_4$
5.5% of NiO
10.4% of $Fe_2O_3$
10.0% of CaO.

Example 2

Batchwise Hydrogenation of 1,3,6-Tricyanohexane 20 g of tricyanohexane, 100 ml of tetrahydrofuran and 4 g of Catalyst A (cf. Example 1) are placed in an autoclave, which is then purged with nitrogen. 30 ml of ammonia are added and the mixture is heated to 60° C. while hydrogen is pumped in to create an internal pressure of 300 bar. The hydrogen is replenished as required. After cooling, decompression, filtration and concentration of the reaction mixture there are obtained, by distillation, 20.5 g of 4-aminomethyl-1,8-diaminooctane (yield 95.2%).

Example 3

Batchwise Hydrogenation of 1,3,6-Tricyanohexane

Example 2 is repeated except that a catalyst is used which has a content of 65.3% of CoO, 5.2% of MnO, 10.3% of $Fe_2O_3$ and 19.2% of $La_2O_3$ and the reaction is carried out at 80° C. There are obtained 21.3 g (98.9%) of 4-aminomethyl-1,8-diaminooctane.

Example 4

Example 2 is repeated except that the reaction is carried out at 170° C. without the use of ammonia. There are obtained 16.9 g of 3-(4-aminobutyl)-piperidine (yield 87.9%).

Example 5

Continuous Hydrogenation of 1,3,6-Tricyanohexane

A trickle-bed reactor having a length of 3 meters and an internal diameter of 16 mm is packed with Catalyst B (cf. Example 1). A 50% solution of 1,3,6-tricyanohexane in tetrahydrofuran is introduced at the top of the reactor. Hydrogen and ammonia are also fed to the top of the reactor and a circulation of 9 l/h is maintained at a tricyanohexane solution feed rate of 500 ml/h and an ammonia feed rate as given below, under a pressure of 300 bar of hydrogen. Three tests are carried out at different temperatures. The discharged reaction mixtures are filtered, concentrated and distilled. The yields are given in the Table below:

| Temp. [°C.] | $NH_3$ Feed [ml/h] | 4-Amino-1,8-di-aminooctane [%] | 3-(4-aminobutyl)-piperidine [%] | Residue [%] |
|---|---|---|---|---|
| 60 | 400 | 97.9 | 1.8 | 0.3 |
| 120 | 200 | 51.2 | 45.3 | 3.5 |
| 170 | 0 | 1.8 | 97.8 | 0.4 |

Example 6

Continuous Hydrogenation of 1,3,6-Tricyanohexane

A bubble column having a length of 2 m and a diameter of 41 mm is packed with catalyst extrudates having a length of 7 mm and a diameter of 4 mm. The catalyst contains the following active components: 70.3% of CoO, 10.5% of NiO, 5.2% of MnO, 14.0% of $Na_2O$. A 40% solution of 1,3,6-tricyanohexane in methanol is introduced at the bottom of the reactor, and hydrogen and ammonia are also fed to the bottom of the column. A circulation of 40 l/h is maintained at a tricyanohexane solution feed rate of 700 ml/h, an ammonia feed rate of 450 ml/h and a hydrogen pressure of 300 bar. The discharged reaction mixture is worked up as described in Example 5. Using a temperature of 80° C., the following yields are obtained: 4-aminomethyl-1,8-diaminooctane 93.7%, 3-(4-aminobutyl)-piperidine 5.3%, residue 1.0%.

We claim:

1. In a process for the preparation of an amine of the formula

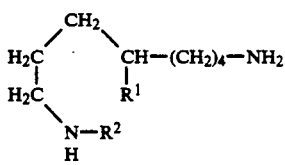

in which $R^1$ is the radical $H_2N-CH_2-$ and $R^2$ is hydrogen, or $R^1$ and $R^2$ together form the bridging group $-CH_2-$, by reacting 1,3,6-tricyanohexane at elevated temperature and pressure with hydrogen in contact with a cobalt-containing catalyst, the improvement which comprises:

carrying out the reaction with a precipitated catalyst which contains
 (a) cobalt oxide, and
 (b) an oxide of a metal selected from the group consisting of alkali metals, alkaline earth metals, the rare earth metals, scandium and yttrium, said precipitated catalyst being activated by partial reduction of the metal oxides to the metals with hydrogen.

2. A process as claimed in claim 1, wherein the catalytic hydrogenation is carried out at a temperature of from 30° to 250° C. and under a pressure of from 50 to 350 bar.

3. A process as claimed in claim 1, wherein, for the preparation of 4-aminomethyl-1,8-diaminooctane, the catalytic hydrogenation of 1,3,6-tricyanohexane is carried out at a temperature of from 30° to 120° C.

4. A process as claimed in claim 1, wherein, for the preparation of 3-(4-aminobutyl)-piperidine, the catalytic hydrogenation of 1,3,6-tricyanohexane is carried out at a temperature of from 120° to 250° C.

5. A process as claimed in claim 1, wherein the catalyst contains, in addition to said cobalt oxide (a) and said metal oxide (b), at least one oxide (c) of an element selected from the group consisting of iron, nickel, manganese, chromium, molybdenum, tungsten and phosphorus.

6. A process as claimed in claim 1, wherein the catalyst contains, in addition to said cobalt oxide (a) and said metal oxide (b), at least one oxide (c) of a metal selected from the group consisting of iron, nickel and manganese.

7. A process as claimed in claim 5, wherein the catalyst contains at least 20% w/w of said cobalt oxide (a), not more than 20% w/w of said metal oxide (b) and up to 60% w/w of said oxide (c) of at least one of the elements iron, nickel, manganese, chromium, molybdenum, tungsten and phosphorus.

8. A process as claimed in claim 6, wherein the catalyst contains from 20 to 95% w/w of said cobalt oxide (a), from 0.5 to 20% w/w of said metal oxide (b) and from 0.5 to 60% w/w of said oxide (c) of at least one of the metals iron, nickel and manganese.

9. A process as claimed in claim 1, wherein the alkali and alkaline earth metal oxides are selected from the group consisting of $LiO_2$, $Na_2O$, $K_2O$, CaO, SrO and BaO and the rare earth metal oxides are selected from the group consisting of $La_2O_3$, $Ce_2O_3$, $Gd_2O_3$, $Dy_2O_3$, $Sm_2O_3$, $Nd_2O_3$ and $Er_2O_3$.

10. A process as claimed in claim 3, wherein the hydrogenation of 1,3,6-tricyanohexane is carried out continuously under a pressure of from 50 to 350 bar for the selective preparation of 4-aminomethyl-1,8-diaminooctane.

11. A process as claimed in claim 10, wherein the reaction temperature is from 50° to 100° C.

12. A process as claimed in claim 10, wherein ammonia is added to the reaction at the rate of 1 to 100 moles per mole of 1,3,6-tricyanohexane to inhibit the formation of 3-(4-aminobutyl)-piperidine.

13. A process as claimed in claim 4, wherein the process is carried out continuously for the selective preparation of 3-(4-aminobutyl)-piperidine.

14. A process as claimed in claim 13, wherein the reaction temperature is from 120° to 200° C.

15. A process as claimed in claim 14, wherein up to 3 moles of ammonia are added to the reaction per mole of 1,3,6-tricyanohexane.

* * * * *

UNITED STATES PATENT AND TRADEMARK OFFICE
CERTIFICATE OF CORRECTION

PATENT NO.  : 5,132,427
DATED       : July 21, 1992
INVENTOR(S) : Koehler et al

It is certified that error appears in the above-indentified patent and that said Letters Patent is hereby corrected as shown below:

Column 6, line 3, claim 9: after "$K_2O$", insert MgO--.

Signed and Sealed this

Tenth Day of August, 1993

Attest:

MICHAEL K. KIRK

Attesting Officer     Acting Commissioner of Patents and Trademarks